United States Patent [19]

Parker et al.

[11] Patent Number: 4,850,690

[45] Date of Patent: Jul. 25, 1989

[54] HEAD-MOUNTED ANALOG RETINA TEST SET

[76] Inventors: William S. Parker, 3210 Corrine Dr., Orlando, Fla. 32803; James C. Bradford, 2117 Buffalo Rd. #285, Rochester, N.Y. 14624

[21] Appl. No.: 226,791

[22] Filed: Aug. 1, 1988

[51] Int. Cl.⁴ .................................................. A61B 3/10
[52] U.S. Cl. ........................................ 351/205; 351/227
[58] Field of Search ............... 351/205, 227, 228, 229, 351/230, 231; 350/145, 146; 29/20, 428

[56] References Cited

U.S. PATENT DOCUMENTS

| | | | |
|---|---|---|---|
| 1,794,571 | 3/1931 | Wrighton et al. | 351/229 |
| 4,236,793 | 12/1980 | Whitney et al. | 351/229 |

Primary Examiner—Rodney B. Bovernick
Assistant Examiner—P. M. Dzierzynski
Attorney, Agent, or Firm—James H. Beusse

[57] ABSTRACT

An eyeglass testing device is provided with independent side-to-side positioning of left and right lenses and independent side-to-side and front-to-back positioning of a separate set of front left and right test lenses on a platform attached with universal adjustment to a head harness and worn by a patient while being tested for vision assistance.

21 Claims, 3 Drawing Sheets

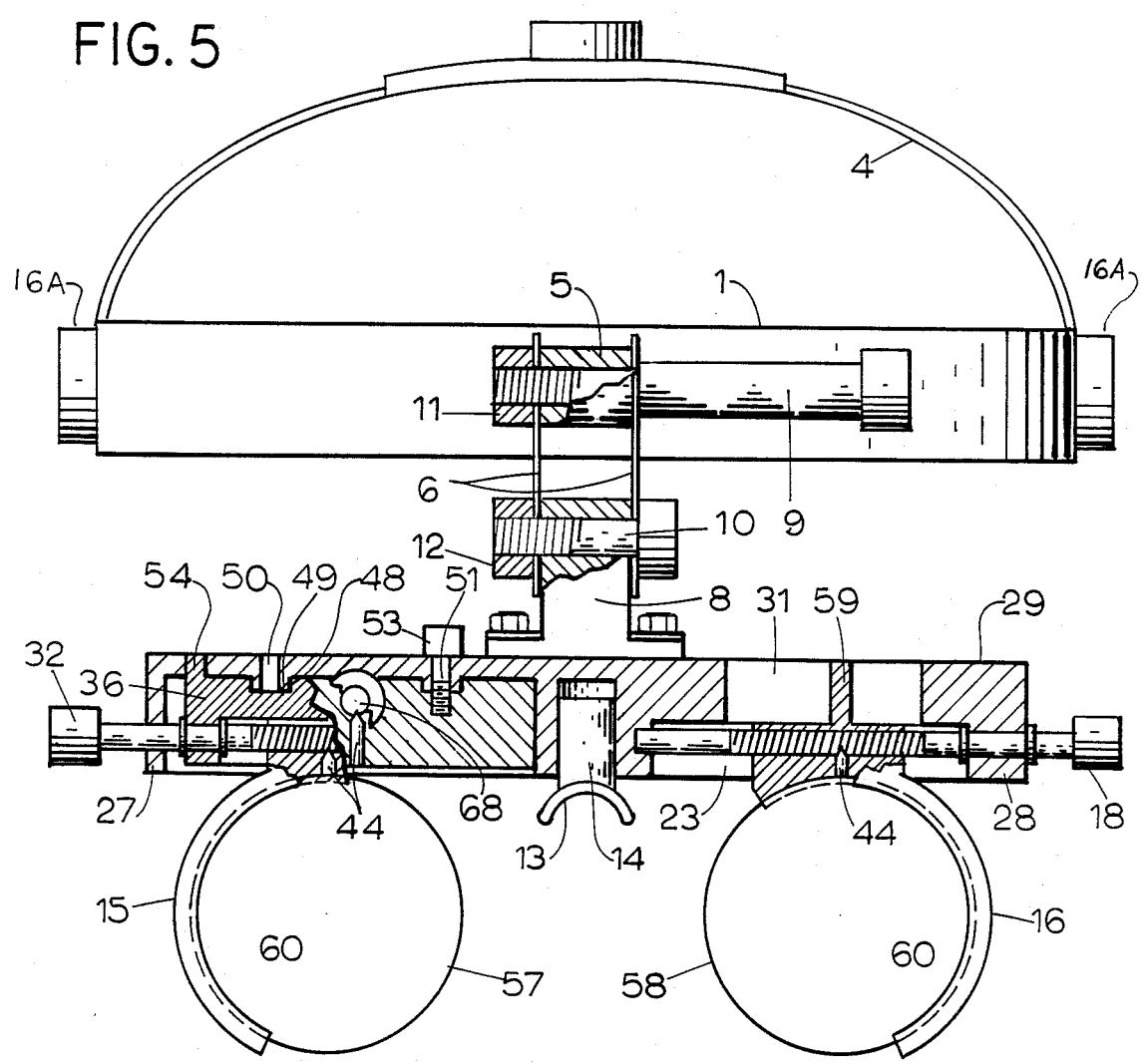

HEAD-MOUNTED ANALOG RETINA TEST SET

BACKGROUND OF THE INVENTION

1. Field of the Invention

This invention relates to test sets for testing vision with analog progressively selected lens settings for determining precise requirements for prescription eyeglasses and for determining viability of a patient's retina, and in particular, to a method and apparatus for measuring requirements for lenses for aiding low vision which has been impaired by macular degeneration, optic nerve damage or similar low-vision problems.

2. Description of the Prior Art

Two main types of test sets for measuring visual acuity have been devised previously and are generally referred to as a surface-mounted or floor-stand type and a test-eyeglass type. Both use incrementally stepped gradations of lens types and corrections that are put into them for testing a person's vision. The more common surface-mounted type has a lens-holder arrangement which can be suspended in front of a patient and includes a plurality of lenses which can be positioned for the patient's use. The patient views a chart through various ones of the lenses, selecting the one which provides the best visual acuity.

The main problem with both of these prior types of lens test sets is that they do not provide for vision testing with continuous variation of lens characteristics. Instead, they provide testing with only stepped variation of lenses. The stepped variation of lens characteristics may miss the optimum selection of dioptric values. Furthermore, these prior art systems may not focus an image on the more optically responsive surfaces of the macular retinal membrane.

Young and healthy eyes generally can adjust to errors and inadequacies resulting from stepped variations in lens selections and from improper focusing. However, when faulty vision is caused either by the degeneration of the whole or a part of the macular retinal membrane on the back of the interior face of the eyeball, or by deterioration of the optic nerves which would normally carry the images from the macular retinal membrane to the brain, more accurate methods than the stepped gradation of lenses is required. The extent of error in focusing and the extent of variation of gradation of test lenses can be so great that the entire vision capacity of a low-vision patient may be missed or distorted with present testing methods.

In some cases, direction of additional light into the eye may be required to achieve even minor vision. Present testing methods do not provide means for testing the effects of reflecting additional light into select portions of the eye nor for testing to determine which parts of the eye may be aided by the reflection of additional light.

The present floor-stand test sets do not provide opportunity to test the effects of changes in incline of the body and the effects of normal light conditions with the test lenses. For patients with low vision, this can be crucial.

Furthermore, present test sets are not believed adequate for identifying viable retina areas in patients suffering from heavy cataracts. It is desirable to be able to identify light responsive retinas in such patients prior to undergoing surgery.

Although the conventional test-eyeglasses method of assessing the effects of lenses with stepped gradations can be employed in normal wearing conditions, the stepped error factor is as great as for the floor-stand type. Moreover, it is very time consuming for both doctor and patient and, therefore, expensive and often psychologically prohibitive. Still further, neither of the present systems provides for relative movement of separate lenses in order to identify the most optically responsive area of eyes with macular degeneration.

SUMMARY OF THE INVENTION

This invention provides analog positioning of a set of front lenses from front-to-back and from side-to-side relative to a set of rear lenses that are analog positionable from side-to-side on an eyeglass test set with optimum positioning suspension from a headpiece in front of the eyes. It enables measurement of sight under continuous variations of lens characteristics. Continuous measurement is referred to as analog measurement as contrasted to stepped measurement. For low-vision patients, the analog method is not only preferable, it is often essential in restoring vision. For assisting less impaired vision, it is more effective and accurate in testing visual acuity than present methods.

Additionally, this invention also provides the advantage of being worn temporarily by patients to test for effect of lens characteristics under various light, distance and angle-of-sight conditions. While it is on a patient, analog variations of lenses and focusing can be made to search out where in the eyes to direct corrections and what types of corrections to be made for maximizing eyesight of the vision-impaired. Thus, it adds features not existing in the prior art and also combines the best characteristics of each of the different types of test sets known in the prior art.

One feature of this invention which is highly significant is that it is far less expensive than others. Not only for the equipment in comparison to the conventional stand type, but for both doctor and patient alike, it requires less time and consequently less cost in the process of providing more accurate and reliable correction and assistance to sight.

In an illustrative embodiment, this invention provides a means of testing for a special type of low-vision correction and assistance made possible by a previous invention by the same inventors. In that previous invention, multiple lenses, typically two lenses known in the trade as "Dualenz," have made it possible for the near-blind to see better. It employs a Galilean-telescope effect from separation of positive and negative refractive lenses and incorporates a unique light-directing ring-prism for image enhancement. A detailed description of these unique eyeglasses in given in U.S. patent application Ser. No. 777,829.

This invention makes it possible to direct images and light precisely on the portions of the eyes most optically functional in low-vision patients in a testing environment whereby the eyeglasses of the aforementioned type may be precisely prescribed and constructed for aiding low-vision patients to see. For testing to aid the normal range of sight deficiency of any level and type of low-vision characteristics, this invention provides the advantages of being universally adjustable in front of a patient's eyes while being tested under normal viewing conditions.

In one form, the present invention includes a headpiece supporting a test set. The headpiece is worn by the patient so as to position the test set adjacent to a patient's eyes and to reduce ambient light glare. The test set includes a housing; left and right rear lens holders suspended in side-to-side sliding contact with a bottom surface of a rearward portion of the housing; left and right front-lens-holder carriers suspended in front-to-back sliding contact with a bottom surface of a forward portion of the housing; left and right front lens holders suspended respectively, in side-to-side sliding contact with a bottom surface of a corresponding one of the front-lens-holder carriers; a headpiece; and means for attaching the housing to the headpiece.

A firm, comfortable headpiece or harness makes it possible for a patient to undergo a full range of effective testing without fatigue. Normally, patients with low vision are older and less capable of being able to undergo a full range of testing with conventional testing methods. With this invention, they are not required to sit up to look into the present floor-stand testing device. In addition, they can raise the test set, relax their eyes and recoup their physical and mental capacity for undergoing further testing. While being tested, they can look around at things they like at varying distances and under varying light and posture conditions. This provides a more complete range of testing and accomplishes it more accurately with less strain, effort, time and cost.

An attachment from the headpiece provides relatively universal positioning of the test set in front of a patient's eyes. It consists of a headpiece swivel mount attached to the front of the headpiece; swivel members fastened in selective vertical-swivel-angle contact with the headpiece swivel mount; adjustment channels in the swivel members; and a housing swivel mount attached to a top surface of the housing and fastenable at selective positions in the adjustment channels. It can be moved in all directions within the required distance range. Up-or-down, side-to-side, closer-or-farther away, it can be moved and set in place initially in relation to the eyes for testing to determine maximum vision assistance. Then when found, an ideal position in front of a person's eyes can be maintained and rested when necessary by a vertical-swivel-channel characteristic in combination with location reference with an adjustable nosepiece which duplicates the panascopic tilt of prescription eyeglasses.

The nosepiece is used only for location, not for supporting the weight of the test set. It consists of a rod with selective length of extension from a cylinder extended between the housing and the nose of a person on whom the eyeglass test set is mounted.

The first step of testing is positioning the centers of left and right rear test lenses an optimum distance from the pupils of a patient's eyes linearly to the axis of optic nerve and pupil of each eye by fixing the head harness snugly and comfortably onto the patient's head with appropriate lengthening of the head strap and head band; by fixing the height and desired horizontal distance of the horizontal distance of the horizontal center of the rear lenses in relation to a patient's eyes by adjusting the swivel connection of the housing to the harness; by adjusting a nosepiece center and length of extension to fit on the patient's nose at a location reference point; selecting rear lenses for particular vision testing and inserting them in the rear lens holders; positioning the vertical centers of the rear lenses independently in relation to plane of vision of each eye by rotating the rear-lens drive rods appropriately to cause the rear lenses to travel from side-to-side selectively; selecting front lenses for particular vision testing and inserting them in the front lens holders; positioning the vertical centers of the front lenses independently in relation to plane of vision of each eye by rotating the side-to-side drive rods for the left and right front lens holders as appropriate to cause selective side-to-side travel of each front lens separately; varying the distances of the left and right front lenses from the left and right rear lenses independently and selectively by rotating the front-to-back drive rods for the left and right front lens-holders as appropriate to cause selective front-to-back travel of each front lens separately.

For impaired-vision characteristics, it is possible with this invention to search and traverse the entire retinal surface to find the most optically functional portions. This is accomplished in conjunction with a set of left and right rear lenses. The left and right front lenses are independently adjustable from side-to-side and from front-to-back. Thus, each eye can be searched, focused, provided with optimum light and tested for vision acuity independently of the other. Such testing can be performed on patients with cataracts prior to surgery to confirm whether surgical removal of cataracts would be beneficial. The light gathering ability of the prism ring can be utilized to direct sufficient light through cataracts so as to verify retinal activity.

Then when lens characteristics for optimum vision assistance are calculated precisely from the continuous analog variation of image refraction and light reflection made available with this invention, precise dioptric and light-reflection prescription features can be determined for wearing glasses. A diopter being a measurement of the refractive power of lenses equal to the reciprocal of focal length in meters, the variation in distance between lenses and from side-to-side enhances accuracy for assisting vision by refracting and focalizing light with greater precision.

An additional unique test method is accomplished by inserting lenses having selective off-set prismatic centers of refractive characteristics in selected lens holders; and rotating such off-set centers appropriately in relation to distance between front and rear lenses and in relation to side-to-side positioning of front and rear lenses for analog scan-testing of vision characteristics of patients. Such lenses can be rotating cylinder (astimatic) lenses to correct for non-spherical eyeballs.

In conjunction with any of the test methods made possible by this invention, use-condition vision can be evaluated and enhanced further by testing vision of patients in such various conditions of light, head tilt, body posture, vision distance and emotional conditions affecting vision as appropriate to further evaluate vision effects of particular lens conditions with the optical test set mounted on a patient; and modifying lens prescriptions to maximize benefits most appropriate for patients.

A unique method of production of the test-set housing includes walls suspended downward from the front, rear, left and right sides of the housing for use as appendages in which to position drive-rod apertures, rear-lens-holder channels and markers. It is a particularly light-weight, low cost and rigid method of construction.

All of these working relationship of parts, use methods, construction methods and more are made available with this invention as will be apparent to those skilled in the art from the accompanying drawings, description and claims.

BRIEF DESCRIPTION OF THE DRAWINGS

For a more complete understanding of the nature, objectives and advantages of the present invention, a detailed description is provided in relation to the accompanying drawings in which:

FIG. 5 is a cutaway front view of the test housing and head harness;

FIG. 6 is a top view of a front-lens carriage;

FIG. 7 is a bottom view of a front-lens carriage;

FIG. 8 is a cross-section from an end of a front-lens carriage from top-to-bottom at point A;

FIG. 9 is a cross-section from an end of a front-lens carriage from top-to-bottom;

FIG. 10 is a cross-section from an end of a front-lens carriage with a front-lens holder positioned at any point of side-to-side travel on the carriage;

FIG. 11 is a cutaway side view of a rear-lens holder; and

FIG. 12 is a top view of the head band of FIG. 1 as an option to the head harness.

DESCRIPTION OF THE PREFERRED EMBODIMENT

Figure 1:
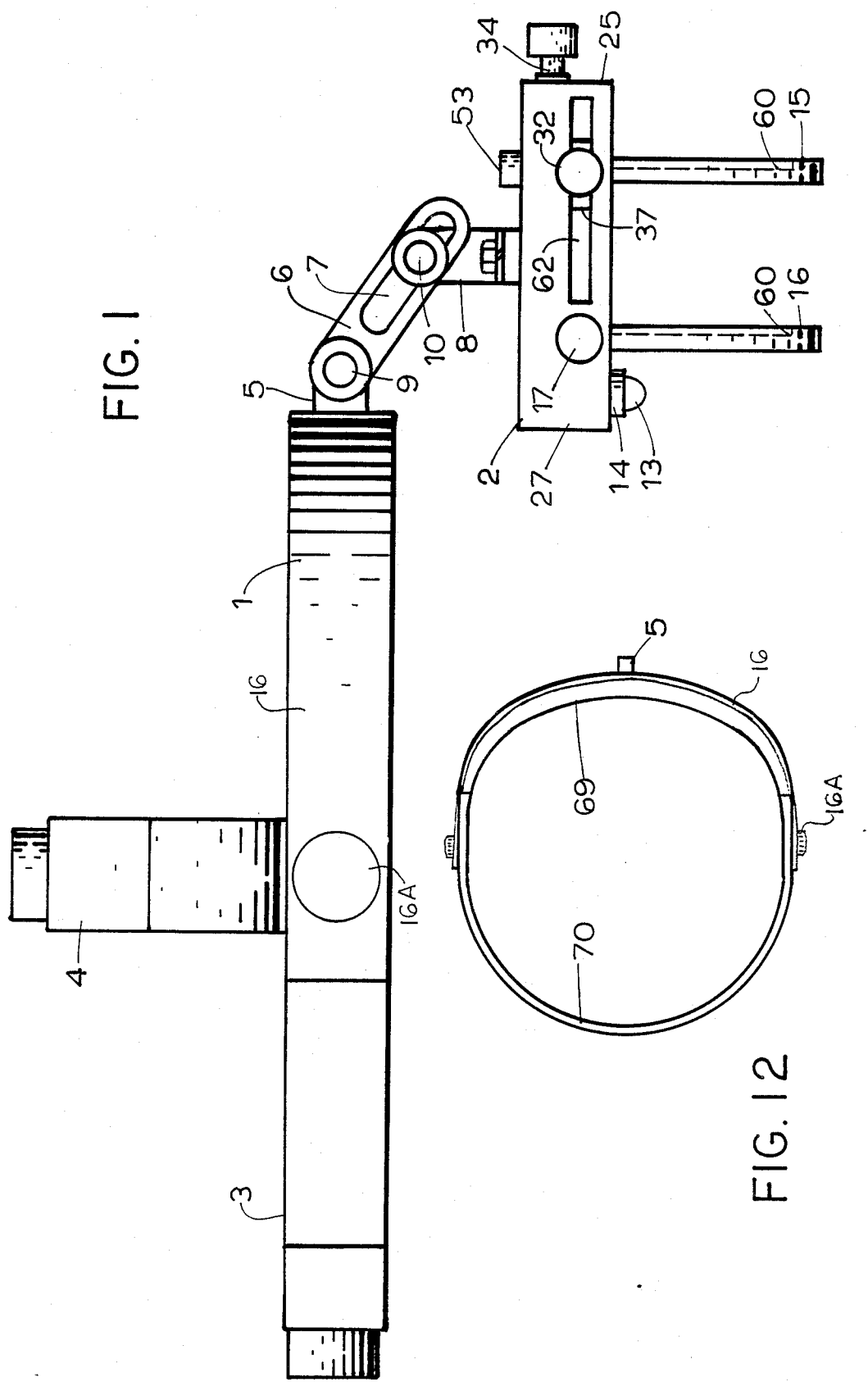
FIG. 1 is a side view showing a test housing adjustably suspended in front of a patient's eyes from the front of a headpiece.

FIG. 1 is a side view of an illustrative form of the present invention showing a headpiece or harness base 1, supporting a test-set housing 2. A harness includes adjustable-length head band 3 and an adjustable head strap 4. A harness swivel mount 5 is attached to the front of the harness base at a position substantially above the nose of the wearer. Attached in vertically-swivelable relationship to the harness swivel mount are swivel members 6 with adjustment channels 7.

The housing 2 in FIG. 1 is swivelably attached to the swivel member with housing swivel mount 8. The harness swivel mount and the housing swivel mount are attached to harness bolt 9 and housing bolt 10 which screw into harness nut 11 and housing nut 12 respectively. The swivel mount 5 may be attached to a movable visor 16 rotatably attached to base 1 by a thumb screw 16A. This visor may be adjusted to relieve pressure on a patient's nose after all other settings are fixed.

FIG. 5 illustrates more completely the connection means of the harness and the housing from a front view. Viewed in combination, FIGS. 1 and 5 show the harness bolt to be long in one optional form for making it accessible for rotating by hand. The housing bolt, however can be short because it is not in a confined location. The harness nut can be attached rigidly to one of the swivel members to hold it in place while tightening or loosening the harness bolt with one hand. It will be noted that the harness bolt is provided with a shoulder section to be snugged up against one of the swivel members. This could also be a retainer washer in a groove around the bolt. The head of the housing bolt provides the same snugging feature. The housing nut can be provided with an appendage riding in the groove to keep it from turning when the housing bolt is tightened or loosened.

It will be seen that this attachment means provides positioning of the housing selectively up, down, inward and outward in relationship to the eyes of a patient for whom vision tests are being made. It is a relatively universal adjustment.

Continuing to refer to FIGS. 1 and 5, a nosepiece 13 with adjustable-extension rod 14 is provided as a reference point for positioning and repositioning the housing with front lens holder 15 and rear lens holder 16. The rod 14 may be held in position by a set screw in the housing. The nosepiece need not support the weight of the housing. When lenses are being changed or when the patient may be resting from vision-testing, the harness bolt can be loosened and the housing swiveled up. When ready to continue testing, the housing can be swiveled down to where the nosepiece again touches the nose as it did for original positioning. This restores the original position of the housing relative to the eyes of the patient.

The first step in using this invention is to position the harness on the head with a circumferential distance around the head, a height position on the head and a central position in relation to the nosepiece. This places the housing where the position of lenses can be adjusted further for each eye and for each eye condition to be tested for optimum vision assistance and correction. It positions the rear lens at the desired distance from the eyes and aligns the horizontal center of the lenses with the horizontal center of the eyes or provides for such variation thereof as desired.

The next step is to position the vertical center of the lenses in line with the vertical center of the eyes or such variation thereof as desired for the particular testing, observation and studies to be performed on a patient. Positioning of the vertical centers of the lenses is accomplished by rotating left-rear lens-holder drive rod 17 and right-rear lens-holder drive rod 18 illustrated in FIGS. 2 and 3.

Figure 2:
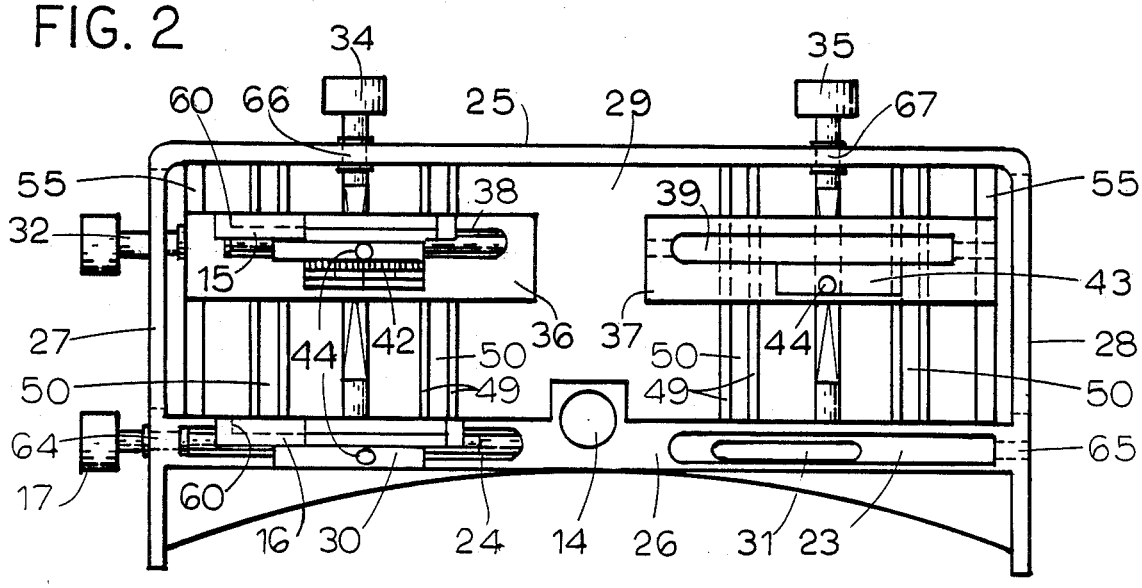
FIG. 2 is a bottom view of the test housing.
Figure 3:
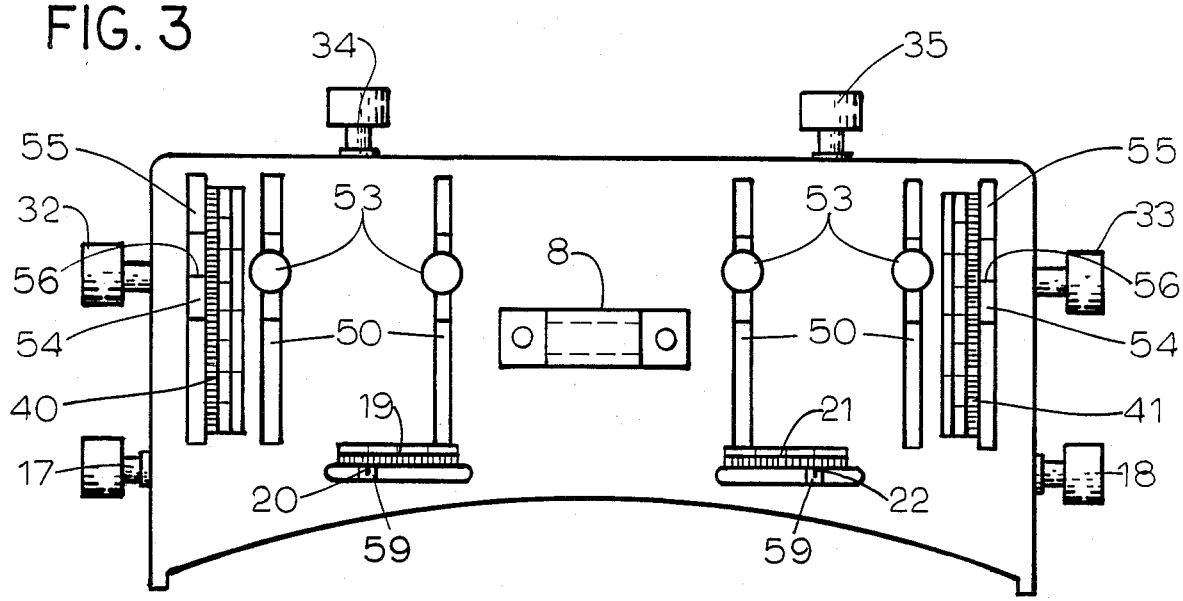
FIG. 3 is a top view of the test housing.

FIG. 2 shows the mechanical working relationship of parts for accomplishing side-to-side movement of the rear lenses from the bottom surface of the housing. FIG. 3 shows the top surface of the housing with a left-rear-lens scale 19 in millimeters with a left-rear-lens-center marker 20 for a left rear lens and a right-rear-lens scale 21 in millimeters with a right-rear-lens center marker 22 for the right rear lens. The right rear lens holder is omitted in FIG. 2 in order to show right-rear-lens-holder channel 23 more completely. Left-rear-lens-holder channel 24 is shown with a rear lens holder in it.

Continuing to refer to FIG. 2, front housing wall 25, rear housing wall 26, left housing wall 27 and right housing wall 28 are suspended down from housing platform 29. The relative distance downward to which each of these walls are suspended is indicated in FIG. 5. Construction of this invention with walls suspended downward from the housing is one method of providing rigidity with light weight. It also provides for appendages in which to position apertures for containing various components such as drive rods. For these reasons, the walled construction of the housing is illustrated as a preferred embodiment. However, rigidity can be provided also by ribbed construction. Appendages with apertures for supporting drive rods can be independent members rather than walls.

It can be observed in FIG. 2 that when wall construction is employed, the rear wall is thicker than the other walls and thicker also than the housing platform. This is to minimize weight wherever it is not required. The rear wall is thicker because it contains right-rear-lens-holder channel 23 and left-rear-lens-holder channel 24.

Through the inward surfaces of these rear-lens-holder channels are extended left and right-rear-lens-holder indicator-bar apertures 30 and 31 respectively.

The front lens can be positioned from side-to-side by rotating left-front-lens side-to-side drive rod 32 and right-front-lens side-to-side drive rod 33 independently for separate side-to-side positioning of the two front lens holders. In addition, the two front lens holders can be positioned independently from front-to-back by rotating left-carrier drive rod 34 and right-carrier drive rod 35 separately.

The front-to-back movement of the front lens holders is accomplished by movement of left-front-lens-holder carrier 36 and right-front-lens-holder carrier 37 from front-to-back. This is illustrated in FIGS. 2, 3 and 5. These front carriers are provided with a left-carrier lens-holder channel 38 and a right-carrier lens-holder channel 39.

It is not necessary to provide front-to-back movement of the rear lenses because the original positioning of the distance of the rear lenses from the eyes accomplishes this step. This positioning can be changed later the same as it was accomplished initially if desired.

Referring to FIGS. 2 and 3, there are metric scales for each of the three movements of the lenses. Two are on the top of the housing and one is on the bottom. On the top of the housing in FIG. 3, they are left-rear side-to-side scale 19, right-rear side-to-side scale 21, left front-to-back scale 40 and right front-to-back scale 41.

On the bottom of the housing, as can be observed in FIG. 2, are left-front side-to-side scale 42 and right-front side-to-side scale 43.

The bottom location of front side-to-side scales requires that the housing be raised to read them. This is not a significant hindrance, however, because these scales will be used less often than other scales after initial positioning. Also, it is very easy to raise the housing to read the side-to-side setting as well as for changing lenses and for allowing a patient to rest for avoiding fatigue.

The length of the scales is twenty millimeters from side-to-side and forty millimeters from front-to-rear. The side-to-side scales are cumulative with respect to each other, however, such that the total variation is equally large for both directions of adjustment. Numbers of millimeters can be shown in addition to lines if desired.

Figure 4:
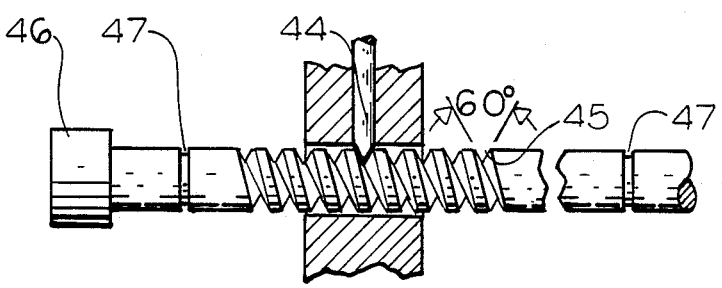
FIG. 4 is a cutaway side view of positioning bolt and anchor pin.

Referring to FIG. 4, all of the lens-adjustment drive rods employ a very light, easily-assembled and inexpensive mechanical system. It is a system also which is easily adjustable for snugness to assure accuracy of the light-duty thread action involved. It is a point-contact of a pointed thread-engagement bolt 44 with matching included-angle between threads 45 on enlarged illustration of drive rod 46. Typically but not necessarily, all of the drive rods have the same diameter, the same thread pitch and the same characteristics of the pointed bolt. The only differences are rod length, thread positioning and positioning of retainer-ring grooves 47.

A variety of well-known ring-and-groove methods for retainer rings can be employed to hold the drive rods in place against traverse action of rotation against the thread-engagement bolts. Construction of steps on the drive rods or on bolt orifices also could be employed in conjunction with retainer rings or nuts. They are referred to generally as linear-traverse-motion-retainer surfaces.

As illustrated in FIGS. 5, 6 and 8, the lens-holder carriers are provided with carrier channels 48 which ride the sides of the split-rails 49 at the bottom surface of the housing platform. Through split-rail apertures 50 are inserted carrier holders 51 which are fastened to the carriers from the top of the housing into carrier-holder apertures 52. The carriers hang under the housing from carrier-holder shoulders 53. Typically, the carrier holders would be threaded bolts, but not necessarily.

Referring to FIGS. 3 and 5, at the top of the outside end of each carrier is a carrier-indicator ridge 54 which is extended vertically through carrier-scale aperture 55 with a carrier-scale indicator 56 to indicate front-to-rear position of each carrier. The marker is in line with the center of the front lens with which vision is being tested, thus indicating exact distance of the front lens from the rear lens at both left and right sides. The distance is indicated, preferably in millimeters, on the left front-to-back scale and on right front-to-back scale.

Referring to FIG. 9, a pointed thread-engagement bolt is shown in a cross-section of a front lens-holder carrier where the pointed thread-engagement bolt is in line with the axis of a drive-rod aperture. This position for thread-engagement bolt is indicated also at the right side of FIG. 2 where it would be covered by the scale that is shown on the left side of the same figure.

Referring to FIG. 10, a pointed bolt for engaging the threads of a drive rod for the front lens holder in side-to-side movement is shown. It utilizes an "L" shape at the base of the lens holder to provide a position from which to insert the thread-engagement bolt at the center of the lens. The central position of the lens is illustrated at the left side of FIG. 5 right above front lens 57. The thread-engagement aperture is the center marker for the left-to-right front scale shown in FIG. 2.

Referring to FIG. 11 in combination with FIGS. 3 and 5, a rear lens holder with rear lens 58 is illustrated with an "L" shape through the base of which a thread-engagement bolt is inserted at an angle. The pointed bolt is at the center of the lens as shown at the right side of FIG. 5. A rear-lens marker rod 59 is extended from the base of the lens holder into the left and right indicator bar apertures marker-rod channel where visible from the top of the housing for the rear lens-holder scales.

Referring to FIGS. 5, 10 and 11, the lens holders are a form of arc clamp. An included arc in front lens holder 15 and in rear lens holder 16 is slightly larger than 180 degrees. Typically, it is 195 degrees or slightly larger than a half circle in order to prevent a lens from sliding out of it through the remaining open portion which is less than a half circle or approximately 165 degrees. The arcs of both clamps are provided with a step base 60 to contain the lenses and to hold them in alignment with the holders.

Referring to FIGS. 7, 8, 9, 10 and 11, a cross-sectional location of carrier side-to-side-drive-rod aperture 61, front-lens-holder drive-rod aperture 62 and rear-lens-holder drive rod aperture 63 are illustrated. FIG. 7 shows the carrier-drive-rod aperture extended both directions beyond a section where the threads in the drive rod will be positioned in assembly.

Referring to FIGS. 1, 2, 3 and 5, positioning of left and right rear-lens-holder-carrier-drive-rod housing apertures 64 and 65 and left and right front-to-back carrier-drive rod housing apertures 66 and 67 are shown. These housing apertures are round for the rear-lens-holder-drive rods and for the carrier-drive rods.

They are long elongated, however, to allow for front-to-back travel of the front-lens-holder drive rod.

Referring to FIGS. 2, 5, 6 and 7, a carrier front-to-back drive-rod aperture 68 is extended from side-to-side through each carrier midway between the carrier channels. In FIG. 3, it is shown in relationship to a thread-engagement bolt at a bottom surface of the right carrier.

Changing of lenses is essential for this invention as well as for the prior art stationary or test-eyeglass types. In this invention, however, sliding analog selection of distance between separate front and rear lenses provides infinite testing and analysis capability. Instead of changing lenses for each step of dioptric gradation of lenses, precise dioptric values can be calculated from the refractive effective of distance between lenses of known values for cutting lenses found to be most optimum for particular vision problems.

In addition, the lenses are rotatable in the lens holders. Rotation in conjunction with analog front-to-back distancing lenses and independent side-to-side movement of lenses provides yet further accuracy in finding and prescribing lenses to maximize optimum vision characteristics of patients.

Changing of lenses will be less frequent for testing with this invention as a result of the analog positioning of the front and rear lenses relative to each other. However, the changes that are made can provide far more information for analysis.

When lenses are changed in the use of this invention, they are easily changed by merely pushing them in or pushing them out of the arc clamp at the opposite side from the step base.

The same lenses can be used in either front or rear lens holders. Additional lenses can be attached with conventional "C" clamps.

The ease of attachment of interchangeable lenses and additional lenses is particularly significant for use of reflective and refractive ring-prism lenses in desired combinations.

There are differences in configuration of the front and rear lens holders for attaching them to their adjustment and indicator means. Primarily, the rear lens holders have a marker rod extended from their base while the front lens holders do not as illustrated in FIGS. 10 and 11.

Referring to FIG. 12 on the same page with FIG. 1, a smaller illustration of the head band of FIG. 1 with preferably cushioned front section 69 and elasticized or adjustable-length back section 70. The movable visor 16 and thumb screws 16A provide ease of adjustment to relieve pressure on the nose of a patient.

A head-band alternative could be fitted with a head strap similar to or the same as the one used for the harness. This could be an embodiment in which, in effect, the same harness would be fitted directly and rigidly to the housing. With the adjustable nosepiece for positioning, it would be similar to the head harness, except for the swivel visor 16 for allowing the patient to rest, for changing lenses easily and for reading the rear side-to-side scale that is under the housing. However, it would not fit and stay in place as well as with the head strap 4 added to the harness.

An eyeglass-temple harness also could be employed as an alternative to the head harness. However, it would not be as adequate as either of the other options. The housing would be slightly lighter for either the head-band option or the eyeglass-temple option because it would not require the swivel-attachment means for the harness option.

What is claimed is:

1. A head-mounted analog eyeglass test set comprising:
    a housing platform;
    left and right rear lens holders suspended in side-to-side sliding contact with a bottom surface of a rearward portion of the platform;
    left and right front-lens-holder carriers suspended in front-to-back sliding contact with the bottom surface of a forward portion of the platform;
    a head harness; and
    a means for attaching the housing platform to the head harness.

2. A head-mounted analog eyeglass test set as described in claim 1 and having rear lens-holder channels at both sides of the center of the rear portion of the housing platform in which the rear lens holders are positioned for side-to-side travel.

3. A head-mounted analog eyeglass test set as described in claim 1 and having front-lens-holder carrier channels at both sides of the center of the front portion of the housing in which the front lens holders are positioned for side-to-side travel.

4. A head-mounted analog eyeglass test set as described in claim 1 and having:
    a set of two split-rail appendages at a bottom surface of the housing platform parallel to left and right edges of both sides of the center of the housing extended from a front portion to a rear portion of the housing;
    carrier channels in the tops of the front lens-holder carriers sized and shaped to receive the split rails for front-to-back travel of the said carriers;
    split-rail apertures extended from the top surface of the housing platform through each split rail throughout the length of each split rail carrier;
    carrier holders with appendages extended from the tops of the carriers through the split-rail apertures; and carrier-holder shoulders extended to the left and right side of each split-rail aperture in sliding contact with the top surface of the housing platform.

5. A head-mounted analog eyeglass test set as described in claim 1 and having:
    a rear-lens-marker aperture extending through the surface of the housing platform from a portion of each rear-lens-holder channel through the length of side-to-side travel of the center of each rear-lens holder;
    a rear-lens-marker rod extended from each rear lens through each rear-lens-marker aperture;
    a carrier-scale aperture parallel to and extended through the left and right sides of the surface of the housing platform for the approximate distance of the carrier-holder apertures;
    a carrier-indicator ridge extended from the top surface of each front-lens-holder carrier through the carrier-scale aperture;
    a front-to-back scale liner to a side of each carrier-scale aperture; and
    a front side-to-side scale linear to a side of each carrier lens-holder channel.

6. A head-mounted analog eyeglass test set as described in claim 1 and having:

a front-lens-holder carrier drive-rod aperture extended from the indicator end to the opposite end of each front-lens-holder carrier;

a front-lens-holder drive-rod aperture extended linearly through a base of each front-lens holder;

a rear-lens-holder drive-rod aperture extended linearly through a base of each rear-lens holder;

a rear-lens-holder-drive-rod housing aperture extended through left and right housing appendages at positions essentially central to the ends of the rear-lens-holder channels;

front-to-back carrier-drive-rod apertures extended from side-to-side of each carrier at a position between the carrier channels;

front-to-back carrier-drive-rod apertures extended concentrically to the front-to-back carrier-drive-rod apertures through left and right side housing appendages;

a lens-holder drive rod extended through each rear-lens holder-drive-rod housing aperture and through the rear-lens-holder drive-rod aperture;

a front-lens-holder drive rod extended in rotatable contact through each carrier-drive-rod housing aperture and carrier-drive-rod aperture;

a carrier drive rod extended in rotatable contact through each carrier-drive-rod housing aperture and front-to-back carrier-drive-rod aperture;

a rear-lens-holder-drive-rod extended in rotatable contact through each rear-lens-holder-drive-rod housing aperture and each rear-lens-holder drive-rod aperture;

linear-transverse-motion retainer surfaces on each drive rod;

a pointed thread-engagement bolt extended from vertical lens-center position in each lens holder to sliding contact with included angle walls of threads on the drive rods that match the included angle of the point of the thread-engagement bolt for each front and rear lens holder; and a pointed thread-engagement bolt extended from a position between the two carrier channels of each front-lens-holder carrier to sliding contact with included-angle walls of threads on the drive rods that match the included angle of the point of the thread-engagement bolt for each front-lens-holder carrier.

7. A head-mounted analog eyeglass test set as described in claim 1 and having:

front and rear arc-clamp lens holders with arcs slightly greater than 180 degrees;

a step base within each arc;

a lens-holder base parallel to the faces of lenses held in the arc clamps of the lens holders;

a drive-rod aperture extended linearly through the base of each lens holder;

a thread-engagement-bolt aperture extended from a vertical center of lenses held in the lens holders to the drive-rod aperture;

a marker rod appendage extended from the base of rear lens holders opposite to the position of the thread-engagement-bolt aperture; and a center marker at the surface of the base of front lens holders opposite to the position of the thread-engagement aperture.

8. A head-mounted analog eyeglass test set as described in claim 1 wherein the rear housing appendage is a rear wall extended downwardly from a rear portion of the housing platform; and rear-lens-holder channels at the bottom surface of the rear wall from which the rear lens holders are suspended for side-to-side sliding contact in relation to the housing platform.

9. A head-mounted analog eyeglass test set as described in claim 1 wherein:

front housing appendages are a front wall extended downwardly from a forward portion of the housing platform;

left housing appendages are a left wall extended downwardly from a left portion of the housing platform; and right housing appendages are a right wall extended downwardly from a right portion of the housing platform.

10. A head-mounted analog eyeglass test set as described in claim 1 and having a nosepiece attached to a rod with selective length extension from a cylinder positioned on the housing adjacent to the nose of a person on whom the eyeglass test set is mounted.

11. A head-mounted analog eyeglass test set as described in claims 1 and having:

a head harness swivel mount attached to the front of the head harness;

swivel members fastened in selective vertical-swivel-angle contact with the harness mount;

adjustment channels in the swivel members; and a housing swivel mount attached to the top surface of the housing and fastenable at selective positions in the adjustment channels.

12. A head-mounted analog eyeglass test set as described in claim 1 and having:

a head harness with an adjustable-length head strap;

an adjustable-length head band; and a cushioned head-harness front piece.

13. A head-mounted analog eyeglass test set as described in claim 1 wherein the adjustable length head strap is removable.

14. A head-mounted analog eyeglass test set as described in claim 1 wherein the head harness is comprised of a set of eyeglass temples attached to the housing.

15. A method of using an eyeglass test set integral with a head harness, the test set including a housing from which test lenses are positioned in separate left and right front and rear lens holders suspended from a test-set housing and positioned independently and selectively in front of a patient's eyes with front-to-back and side-to-side rotatable drive rods for the front lenses and side-to-side rotatable drive rods for the rear lenses; the head harness including an adjustable head band around and an adjustable head strap that is attachable over a patient's head; a vertically and front-to-back horizontally adjustable swivel connection of the housing to the harness; and an adjustable-length nosepiece extended from the housing adjacent to the nose of a patient being tested;

positioning the centers of left and right rear test lenses an optimum distance from the pupils of a patient's eyes linearly to the axis of optic nerve and pupil of each eye by fixing the head harness snugly and comfortably onto the patient's head with appropriate lengthening of the head strap and head band; by fixing the height and desired horizontal distance of the horizontal center of the rear lenses in relation to a patient's eyes by adjusting the swivel connection of the housing to the harness; and by adjusting a nosepiece center and length of extension to fit in the patient's nose at a location reference point;

selecting rear lenses for particular vision testing and inserting them in the rear lens holders;

positioning the vertical centers of the rear lenses independently in relation to place of vision of each eye by rotating the rear-lens drive rods appropriately to cause the rear lenses to travel from side-to-side selectively;

selecting front lenses for particular vision testing and inserting them in the front lens holders;

positioning the vertical centers of the front lenses independently in relation to plane of vision of each eye by rotating the side-to-side drive rods for the left and right front lens holders as appropriate to cause selective side-to-side travel of each front lens separately; and varying the distances of the left and right front lenses from the left and right rear lenses independently and selectively by rotating the front-to-back drive rods for the left and right front lens holders as appropriate to cause selective front-to-back travel of each front lens separately.

16. The method of claim 15 and further comprising:
determining location on the retina of optical vision-imaging capacity of each eye of a patient for alignment of axis-of-vision with appropriate lenses by analog scan-testing of vision axes of retina and pupil surfaces; and prescription of wearing eyeglass lenses which focus images on such retina locations.

17. The method of claim 15 and further comprising:
varying the distances of front lenses from rear lenses progressively to determine dioptric power of lenses to be prescribed for optimum vision for each eye of a patient on an accurate analog basis.

18. The method of claim 15 and further comprising:
inserting a front lens having a prismatic ring with positive light reflection at its circumferential periphery, an optical prism and an optical center;

inserting a rear lens having a prismatic ring with negative light reflection at its circumferential periphery, an optical prism and an optical center;

analog scan-testing of retinal surfaces for portions with maximum optical responsiveness with increased illumination from added light reflection in conjunction with optimal refractive image-enhancement for vision-impaired patients; and designing multiple-prism lenses having light-reflection in addition to image-refraction directed appropriately at the portions of eyes having maximum capability of transmitting image detection through optic nerves of vision-impaired patients.

19. The method of claim 15 and further comprising:
inserting the lenses having selective off-set prismatic centers of refractive characteristics in selected lens holders; and rotating such off-set centers appropriately in relation to distance between front and rear lenses and in relation to side-to-side positioning of front and rear lenses for analog scan-testing of vision characteristics of patients.

20. The method of claim 15 and further comprising:
testing vision of patients in such various conditions of light, head tilt, body posture, vision distance and emotional conditions affecting vision as appropriate to further evaluate vision effects of particular lens conditions with the optical test set mounted on a patient; and modifying lens prescriptions to maximize benefits most appropriate for patients.

21. A method for manufacturing an optical test set integral with a head harness, the optical test set including a housing from which front and rear test lenses are suspended and moved selectively in front of a person's eyes, the head harness including a head band attached snugly to the person's head and an adjustable connection between the head harness and the housing;

forming a housing platform with walls suspended downward from its edges; the width of the platform being approximately equal to the width of an eyeglass frame and the length being determined by the distance from the eyes from which test lenses may be suspended; a left-end wall, a right-end wall and a front-wall being extended a selective distance downward from the top surface of the platform; the thickness of the platform being as thin as possible for light weight and rigidity with the construction materials used; and a rear wall being wide enough to contain mechanisms for sliding rear lens holders from side-to-side;

forming left and right rear lens-holder channels in the rear wall at a select distance between the center and the outside of the platform and being sized and shaped to allow side-to-side movement of rear test-lens holders in the channels in front of a patient's eyes;

forming two rear lens holders having arc-spring clamps with a step matching the diameter of lenses to be held in the arcs of the arc-spring clamps; a rectangular lens-holder base sized and shaped on each lens holder to fit snugly in the rear-lens-holder channels for being moved from side-to-side in front of a patient's eyes; an indicator bar extended from the base of each rear lens holder in a direction opposite the arc-spring clamps and positioned linearly to the center of the lens to be held in the clamp; and a thread-engagement-bolt aperture with a tapped thread extending from the lens side of each base to a drive-rod cylinder in each rear-lens-holder base;

forming two rear-lens-indicator apertures through the platform parallel to the two rear-lens-holder channels;

forming round rear-lens-holder side-to-side drive-rod orifices in the left and right end walls of the housing at positions in which the centers of such control-rod orifices are spaced between the walls of each of the two rear-lens-holder channels;

forming two rear-lens side-to-side drive rods having a threaded portion on each with included angles between thread walls matching included-angle ends of thread-engagement bolts; retainer-ring grooves for retainer rings to arrest transverse motion of the drive rods when rotated against thread-engagement bolts in the rear lens holders and; handle sections for each drive rod;

forming left and right sets of two split-rail carrier appendages extended at right angles perpendicularly from the bottom surface of the platform and parallel to the left and right ends of the platform at positions which allow left and right carriers of lens holders suspended therefrom to be moved selectively from front-to-back in front of a patient's eyes;

forming two sets of two front carrier-holder apertures and two carrier-indicator apertures in the surface of the platform extended between the front and rear walls of the housing parallel to its left and right ends at positions in the center of each split-rail carrier appendage for selective sliding movement of carrier-holders in the apertures and at positions near the outside walls of the housing for measurement of sliding travel of front-lens-holder carrier indicators;

forming four carrier holders having carrier-holder appendages extended from rigid contact with the carriers through the carrier-holder apertures and shoulders which support carriers attached to the carrier holders in sliding contact with the top surface of the housing at each carrier-holder aperture;

forming left and right front-lens-holder carriers having a carrier-position read-out ridge at one end; rail channels to match the two split-rail appendages under the left side of the housing in the left front lens carrier; rail channels to match the two split-rail appendages under the right side of the housing in the right front lens carrier; a front-lens-holder channel in the front side of each carrier; a front-to-rear drive-rod aperture extended from front-to-back of each carrier and positioned between the rail channels; side-to-side drive-rod apertures positioned in the outside end of each lens-holder carrier; and a thread-engagement-bolt aperture positioned to engage each carrier with threads of a front-to-back thread-engagement bolt;

forming two front lens holders having arc-spring clamps with a step matching the diameter of lenses to be held in the arcs of the arc-spring clamps; a rectangular lens-holder base sized and shaped on each front-lens holder to fit snugly in the front-lens-holder carrier channels for being moved from side-to-side independently of side-to-side movement of the rear lens holders in front of a patient's eyes; an indicator mark on each front lens holder positioned linearly to the center of the lens to be held in the arc clamp; and a thread-engagement-bolt aperture with a tapped thread extending from the lens side of each base to drive-rod cylinder in each front-lens-holder base;

forming side-to-side carrier-drive-rod apertures sized and shaped in the left and right walls of the housing to allow front-to-back movement of side-to-side carrier drive rods extended from the carriers;

forming side-to-side front-lens-holder drive rods having a threaded portion on each with included angles between thread walls matching included-angle ends of thread-engagement bolts; retainer-ring grooves for retainer rings to arrest transverse motion of the drive rods when rotated against the thread-engagement bolts in the front lens holders; and handle sections for each drive rod;

forming front-to-back carrier-drive rods having a threaded portion on each with included angles between thread walls matching included-angle ends of thread-engagement bolts; retainer-ring grooves for retainer rings to arrest transverse motion of the drive rods when rotated against thread-engagement bolts in the front-lens carriers;

forming left and right front-to-back carrier-drive-rod apertures in the front and rear walls of the housing sized and shaped at positions which allow insertion of front-to-back carrier-drive rods through matching apertures in the front lens-holder carriers;

forming thread-engagement bolts sized and shaped to match each thread-engagement bolt aperture in the two rear lens holders, in the two front lens holders and in the two front lens-holder carriers;

forming a rear-lens side-to-side read-out scale at the top surface of the housing platform where the rear-lens-holder indicator is extended from the rear-lens holder through the rear-lens-holder indicator aperture;

forming a front-lens front-to-back read-out scale at the top surface of the housing platform where the front-lens-carrier position-read-out ridge is extended from each of the two carriers through the carrier-read-out-ridge aperture;

forming a front-lens side-to-side read-out scale at the bottom surface of each front lens-holder carrier where the front lens holders are attached slidably to their carriers beside the side-to-side travel of the front-lens-holder indicator marker;

forming a nosepiece cylinder housing positioned centrally between the forming a nosepiece having a member extendible from the nosepiece-cylinder housing for position setting of the nosepiece at selective distances from the housing;

forming a head harness having an adjustable length head band; a solid mounting portion overlayed over cushioning material at the front; and an optionally attachable head strap that is adjustable in length;

forming a swivel harness connector with channeled swivel-connection extension from the solid portion of the head mount;

forming a swivel housing connector fastenable to the channeled swivel-connection extension;

inserting a harness bolt through the swivel harness connector from one side and tightening it with a nut at the opposite side;

inserting a housing bolt through the swivel housing connector from one side and tightening it with a nut at the opposite side;

inserting the rear base of each rear lens holder into each rear-lens-holder channel with the open side of each arc clamp facing the center of the housing and the rear-lens indicator bar extending into the rear-lens indicator aperture;

inserting each rear-lens side-to-side drive rod into the rear-lens drive-rod orifices and fixing them in place with retainer rings at each side of the end wall of the housing through which they are inserted;

inserting a rear-lens-holder thread-engagement bolt into each rear-lens-holder thread-engagement-bolt aperture to engage the threads on each of such drive rods in snugly-sliding contact;

positioning left and right side-to-side front-lens-holder carriers onto the bottom surface of the housing platform with the left set of two split-rail appendages in the carrier channels of the left carrier, the right set of two split-rail appendages in the carrier channels of the left carrier, the left carrier-indicator ridge extended through the left indicator-ridge aperture and, the right carrier-indicator ridge extended through the right indicator-ridge aperture;

inserting a front-lens front-to-back drive rod into each front drive-rod orifice and into the front-toback drive-rod aperture in each front-lens-holder carrier;

inserting thread-engagement bolts into thread-engagement-bolt orifices to engage the drive rod in each carrier;

inserting left and right front-lens holder bases into the left and right front-lens-holder carriers respectively with the open side of each arc clamp facing the center of the housing;

inserting thread-engagement bolts into thread-engagement-bolt orifices to engage the drive rod in each front lens holder; and positioning retainer rings in the retainer-ring grooves of each drive rod to arrest linear travel of the drive rods when rotating them against the thread-engagement bolts of each drive rod.

* * * * *